(12) United States Patent
Chen et al.

(10) Patent No.: US 7,595,882 B1
(45) Date of Patent: Sep. 29, 2009

(54) HOLLOW-CORE WAVEGUIDE-BASED RAMAN SYSTEMS AND METHODS

(75) Inventors: Rui Chen, Clifton Park, NY (US);
Marko Klaus Baller, Saarbrücken (DE);
Peter Joseph Codella, Niskayuna, NY (US);
Anis Zribi, Rexford, NY (US);
Renato Guida, Wynantskill, NY (US);
Alexey Vasily Vert, Schenectady, NY (US);
Radislav Alexandrovich Potyrailo, Niskayuna, NY (US);
Xiaoyong Liu, Malden, MA (US);
Zhiyong Wang, Clifton Park, NY (US)

(73) Assignee: Geneal Electric Company, Niskayuna, NY (US)

( * ) Notice: Subject to any disclaimer, the term of this patent is extended or adjusted under 35 U.S.C. 154(b) by 0 days.

(21) Appl. No.: 12/102,079

(22) Filed: Apr. 14, 2008

(51) Int. Cl.
*G01N 21/00* (2006.01)
(52) U.S. Cl. ...................... 356/437; 356/301
(58) Field of Classification Search .......... 356/301, 356/437
See application file for complete search history.

(56) References Cited

U.S. PATENT DOCUMENTS

| | | | |
|---|---|---|---|
| 6,343,174 B1 | 1/2002 | Neuberger | |
| 6,777,244 B2 | 8/2004 | Pepper et al. | |
| 6,850,657 B2 | 2/2005 | Dhadwal et al. | |
| 6,900,890 B1 | 5/2005 | Rice | |
| 7,283,712 B2 | 10/2007 | Shaw et al. | |
| 2004/0069948 A1 | 4/2004 | Feisst et al. | |
| 2004/0208213 A1* | 10/2004 | Lichtenstein et al. | 372/43 |
| 2005/0287696 A1 | 12/2005 | Dumais et al. | |
| 2006/0193552 A1 | 8/2006 | Sugita | |
| 2006/0193583 A1* | 8/2006 | Dong et al. | 385/127 |
| 2006/0233481 A1 | 10/2006 | Li | |

FOREIGN PATENT DOCUMENTS

| | | |
|---|---|---|
| EP | 1653216 A2 | 5/2006 |
| WO | WO2004001465 A1 | 12/2003 |

OTHER PUBLICATIONS

Buric et al., "Enhanced Spontaneous Raman Scattering and Gas Composition Analysis Using a Photonic Crystal Fiber", Aug. 6, 2008, vol. 47, No. 23, Applied Optics, pp. 4255-4261.

* cited by examiner

*Primary Examiner*—Gregory J Toatley, Jr.
*Assistant Examiner*—Abdullahi Nur
(74) *Attorney, Agent, or Firm*—Joseph J. Christian

(57) ABSTRACT

Embodiments of the invention include a system for sensing homonuclear diatomic molecules, such as, for example, nitrogen. Other embodiments include a method for sensing homonuclear diatomic molecules. The system may include a light source, a hollow-core wave-guiding device that exhibits a low attenuation at predetermined operating optical frequencies and is in optical communication with the light source, a gas introduction system for introducing a gaseous medium between the light source and the hollow-core wave-guiding device, and a detector in optical communication with the hollow-core wave-guiding device.

10 Claims, 6 Drawing Sheets

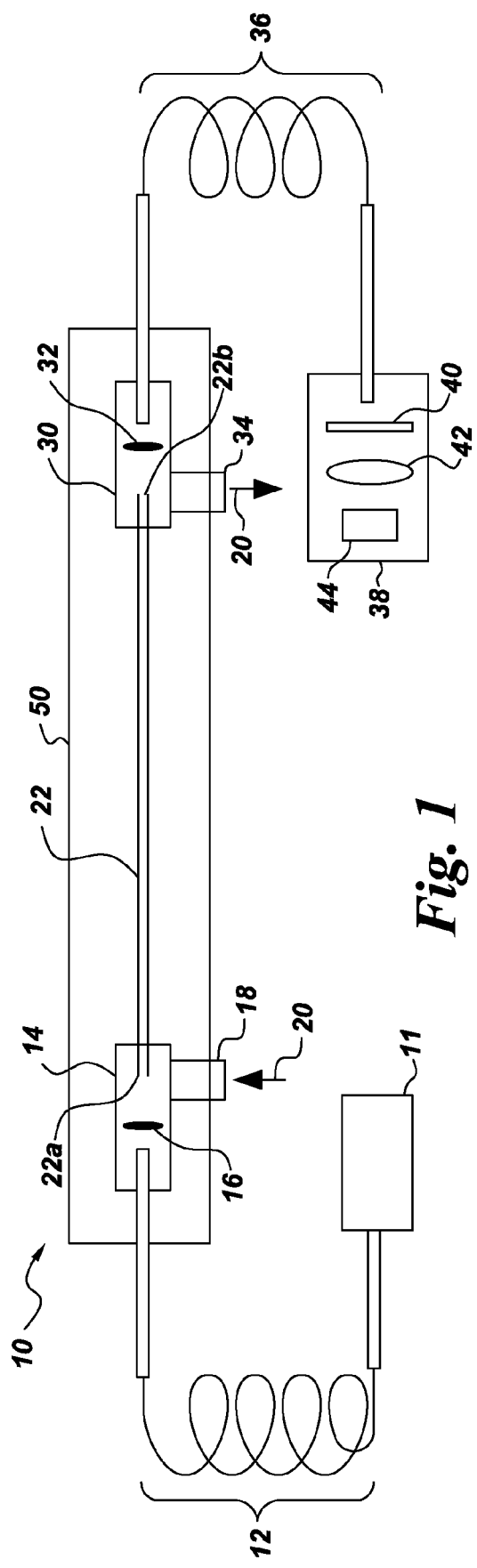
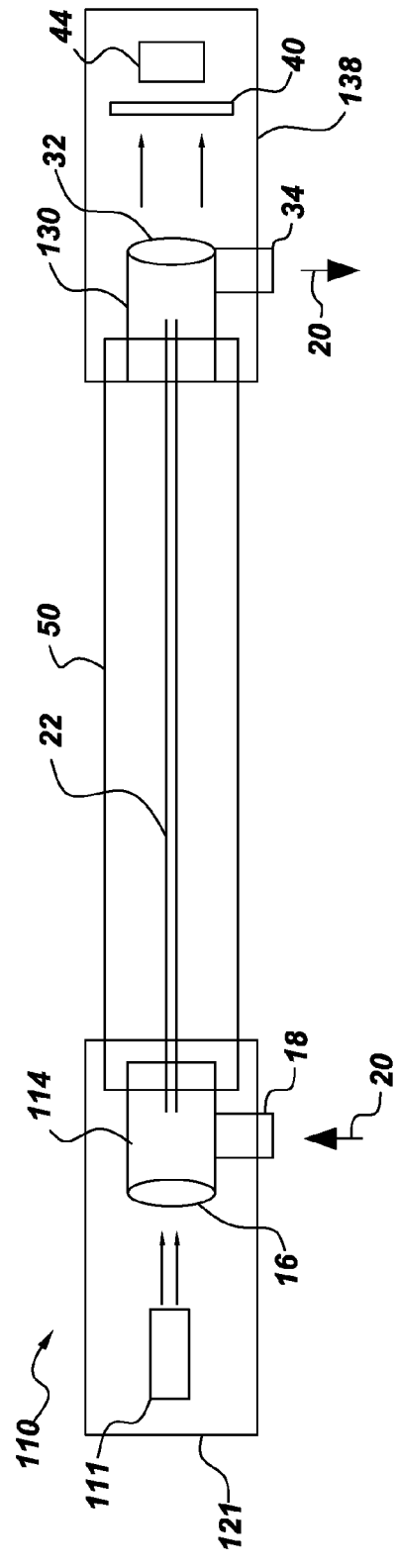
Fig. 1
Fig. 2

HOLLOW-CORE WAVEGUIDE-BASED RAMAN SYSTEMS AND METHODS

BACKGROUND

The invention generally relates to a gas sensing system and method, and more particularly to a hollow-core waveguide-based Raman system and method.

Homonuclear diatomic molecules are generally difficult to detect and measure. Such molecules as nitrogen and hydrogen, for example, do not absorb light under standard pressure and temperature conditions. They are, therefore, difficult if not impossible to detect and quantify with optical absorption based techniques. Further, oxygen has a weak forbidden absorption band that is difficult to use for reliable quantitative measurements. Most common analytical methods are based on low temperature gas chromatography.

There are few reliable techniques known for high accuracy and precision detection and quantification of such molecules. Due to the symmetry of such molecules, they are Raman active, making it possible to identify these molecules with high selectivity based on their Raman spectral peaks.

Raman sensing is widely applied for detection of various chemical compounds and biomaterials. Raman spectroscopy measures the frequency change and intensity of inelastically scattered light from interaction between molecules and monochromatic light. The spectral shift of Raman scattering can be associated with the interaction of an incoming photon and the molecule. The photon loses or gains energy interacting with specific vibrational, rotational, or electronic energy states of the molecule. It is therefore possible to identify molecules from their Raman peak positions, which indicate various molecular energy levels. Raman scattering is a function of the incident light power ($I_0$), the inverse wavelength ($\lambda$) of the incident light to the $4^{th}$ power, the concentration of material in the beam (c), and the scattering cross section of the molecule (J). In addition, any experimental setup and/or sample has its own restrictions on the ability of the instrument to collect and analyze light. This factor is usually called the instrument factor (K). Therefore, a simplified equation for the observed Raman Scatter can be expressed as follows:

$$R = I_0 c J K / \lambda^4 \quad \text{Eqn. (1)}$$

Clearly, if the experimental conditions are controlled, Raman spectroscopy should be capable of quantitative analysis, i.e., the intensity of a Raman signal is proportional to the partial pressure or concentration of the molecule. The Raman cross section is multiplied by a concentration factor. For many Raman samples, the factor is essentially one for a solid or liquid. For a gas sample, the factor is approximately $4.5 \times 10^{-5}$. Therefore, Raman sensing of low-density media such as gases is very challenging. Strong laser power around watt level and high gas pressure from 50 to 100 atmospheres are usually employed. Also, quantification of the concentrations of gas components in a mixture requires strong signals, especially at low concentrations. Therefore, enhancing techniques are required to produce and collect Raman scattered photons from a mixture of gases.

Raman signals are intrinsically weak, roughly ten to sixteen orders of magnitude smaller than fluorescence. To achieve lower detection limits, surface enhanced Raman (SERS) and/or resonance Raman have been used to improve the Raman signal of certain chemicals. SERS requires absorbing the target molecules onto a roughened metal surface. Resonance Raman requires strong coupling between vibrational and electronic levels; therefore, they are not universal.

One known method for increasing the intensity of a Raman signal is Coherent anti-Stokes Raman Spectroscopy (CARS), which is a nonlinear optical method using two or more intense beams of light to generate anti-Stokes blue-shifted Raman signals. CARS experiments are not routine and are strongly dependent on the reproducibility of the performance of expensive lasers. See, for example, Begley, R. F., et al., "Coherent anti-Stokes raman spectroscopy, Applied Physics Letters, 25, 387 (1974). Much emphasis has therefore been placed on improving the interactions between light and gas analytes, which usually involves a multi-pass arrangement where the illumination laser beam is focused on the sample volume from a variety of directions. Gains of 10 to 100's are about all that is possible from this approach. This approach, however, has its limitation in that optical mirrors are susceptible to contamination. Loss of power is inversely proportional to reflectivity to the power of the number of reflections. Even for moderately efficient cells, the number of reflections can be between 25 and 100 therefore even very mild contamination can have devastating effects on cell efficiency.

Photonic bandgap fibers are known and commercial products in certain ranges are available. See www.crystal-fibre.com. These fibers employ a central hollow core surrounded by a honeycomb structure. Contrary to traditional fiber optics that relies on refractive index difference to guide light, photonic band gap fibers guide light based on the band gap created by periodic structure of air holes. More than 95% of the light is guided through the central core. See, G. Humbert, J. C. Knight, G. Bouwmans, P. S. J. Russell, D. P. Williams, P. J. Roberts, and B. J. Mangan, "Hollow core photonic crystal fibers for beam delivery," Opt. Express 12, 1477-1484 (2004); Russell, P. "Photonic crystal fibers", Science, 299, 358-262. 2003. The dimensions of both the core and honeycomb can be customized to yield fiber specifically tuned to a particular wavelength. Guiding light in the hollow core holds many applications that were not possible before. It has been used for IR absorption measurement of weak absorbing gases. See, T. Ritari, J. Tuominen, H. Ludvigsen, J. Petersen, T. Sørensen, T. Hansen, and H. Simonsen "Gas sensing using air-guiding photonic bandgap fibers", Optics Express, Vol. 12, Issue 17, pp. 4080-4087. Particularly for Raman spectroscopy, the hollow core provides long interaction lengths between gas and laser while keeping the laser beam tightly confined in a single mode. The photon intensity inside the hollow core is very large due to the micron-size space. This has the potential of greatly enhancing the gas phase spectrum of nitrogen or any other contained gas. For example, see U.S. patent publication 2006/0193583. Further, the use of photonic bandgaps in a Raman device is also known. See, for example, U.S. Pat. No. 7,283,712 (hereinafter, "the Shaw patent"). The Shaw patent discloses a gas filled hollow core chalcogenide photonic bandgap fiber Raman device. The specific Raman device of the Shaw patent is designed for infrared light. Further, the specific Raman device of the Shaw patent includes a doped portion.

One homonuclear diatomic molecule, nitrogen, is a critical component found in natural gas. The development of an approach that would enable direct measurement of nitrogen would be critical in developing an inferential energy meter for the natural gas industry. It would therefore be advantageous to develop a new approach to detecting and quantifying homonuclear diatomic molecules.

SUMMARY

One embodiment of the invention described herein is directed to a system for sensing nitrogen. The system includes a light source and a hollow-core wave-guiding device that exhibits a low attenuation at predetermined operating optical frequencies. The hollow-core wave-guiding device is in optical communication with the light source. The system also includes a gas introduction system for introducing a gaseous medium between the light source and the hollow-core wave-guiding device and a detector in optical communication with the hollow-core wave-guiding device.

Another embodiment of the invention is directed to a system for sensing homonuclear diatomic molecules. The system includes a light source, an undoped hollow-core wave-guiding device in optical communication with the light source, a lens positioned between the light source and the undoped hollow-core wave-guiding device, and a gas introduction system for introducing a gaseous medium between the light source and the hollow-core wave-guiding device. The system also includes a detector in optical communication with the hollow-core wave-guiding device and a filter positioned between the undoped hollow-core wave-guiding device and the detector.

Another embodiment of the invention is directed to a system for sensing homonuclear diatomic molecules. The system includes a light source and a hollow-core wave-guiding device in optical communication with the light source. The system also includes a gas introduction system for introducing a gaseous medium between the light source and the hollow-core wave-guiding device and a detector in optical communication with said hollow-core wave-guiding device. The hollow-core wave-guiding device is configured to transmit in the visible range of the light spectrum.

Another embodiment of the invention is a method for sensing homonuclear diatomic molecules. The method includes transmitting light from a light source through a hollow-core wave-guiding device that exhibits a low attenuation at predetermined operating optical frequencies, introducing a gaseous medium between the light source and the hollow-core wave-guiding device, and detecting homonuclear diatomic molecules within the gas.

Another embodiment of the invention is a method for optical measurement of at least one analyte in a sample. The method includes exciting light into a photonic crystal fiber at excitation conditions that control non-analyte related emission of secondary radiation.

These and other advantages and features will be more readily understood from the following detailed description of preferred embodiments of the invention that is provided in connection with the accompanying drawings.

BRIEF DESCRIPTION OF THE DRAWINGS

FIG. 1 is a schematic view of a sensing system constructed in accordance with an embodiment of the invention.

FIG. 2 is a schematic view of another sensing system constructed in accordance with an embodiment of the invention.

DETAILED DESCRIPTION OF EMBODIMENTS OF THE INVENTION

Figure 3:
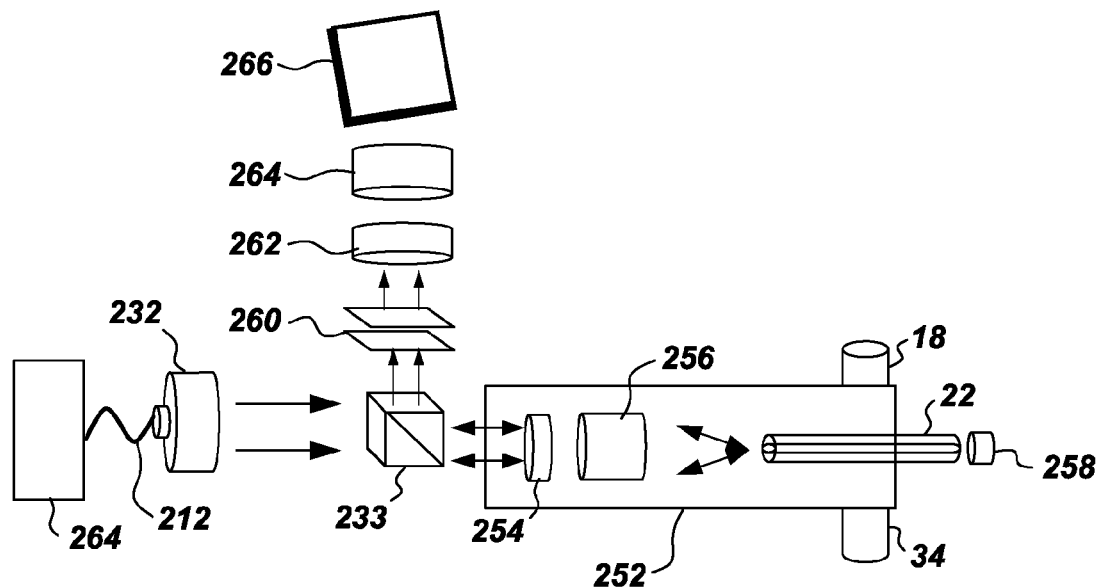
FIG. 3 is a schematic view of another sensing system constructed in accordance with an embodiment of the invention.

Referring to FIG. 1, there is shown a sensing system 10 with a laser 11, a photomultiplier within a housing 38, and a photonic crystal fiber assembly within a housing 50. The laser 11 is in optical communication with the photonic crystal fiber assembly through a fiber apparatus 12, which optically couples the laser 11 with a lens 16 within an integrated lens housing 14. A photonic crystal fiber 22 is placed such that one end $22_a$ is within the integrated lens housing 14 on a side of the lens 16 opposite from the fiber apparatus 12. Positioned between the lens 16 and the end $22_a$ of the photonic crystal fiber 22 is an inlet 18 to allow a flowing liquid or gaseous medium 20, such as natural gas, to flow into the integrated lens housing 14.

Figure 4:
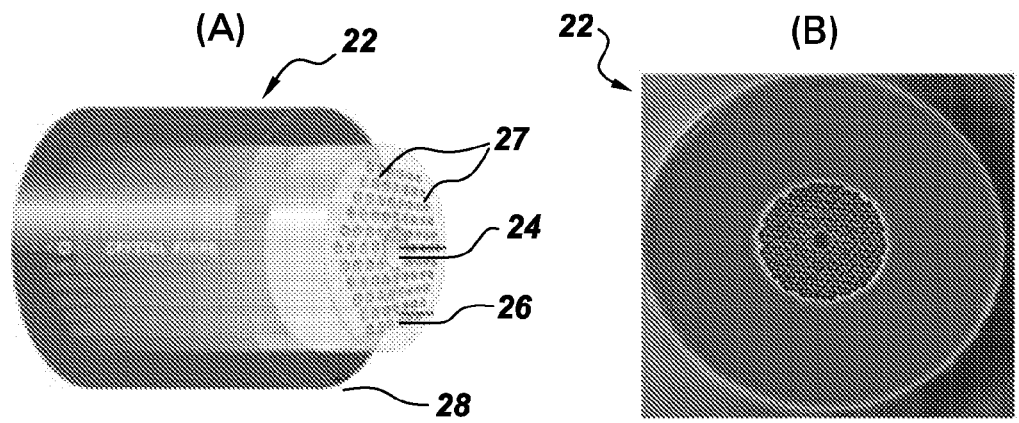
FIGS. 4A and 4B are views illustrating a photonic crystal fiber used in the sensing systems of FIGS. 1-3.

With specific reference to FIGS. 4(A) and (B), the photonic crystal fiber 22 includes a hollow, or air, core 24 surrounded by a cladding 26 and a coating 28. The cladding 26 includes numerous openings 27. The air core 24 provides long interaction lengths between the natural gas 20 and the laser 11, while also keeping the beam of the laser 11 tightly confined in a single mode. The photon intensity inside the air core 24 is large due to the micro-size space.

The opposite end $22_b$ of the photonic crystal fiber 22 of FIG. 1 is in optical communication with a lens 32 within a second integrated lens housing 30. Positioned between the lens 32 and the end $22_b$ of the photonic crystal fiber 22 is an outlet 34 to allow the natural gas 20 to flow out of the integrated lens housing 30. The photomultiplier within the housing 38 is optically coupled to the photonic crystal fiber 22 through a second fiber 36. The housing 38 includes a lens 42 positioned between a filter 40 and a detector 44, such as a photomultiplier.

The photonic crystal fiber 22 is designed to exhibit a low attenuation at the operating optical frequencies. This may exponentially enhance Stokes scattering while also reducing the required power threshold for the excitation photon source for stimulated Raman scattering to occur. Further, the photonic crystal fiber 22 provides a long optical path for interaction between the beam from the laser 11 and chemical molecules, enabling the confinement of the isotropic Raman photons to a two-dimensional structure for more efficient signal collection. While the sensing system 10 has been described as including a photonic crystal fiber 22, any hollow-core, wave-guiding device that exhibits a low attenuation at the operating optical frequencies would be suitable. Such alternative hollow-core, wave-guiding devices may include hollow-core capillaries with dielectric coatings for lessening optical losses within the spectral range of interest. See, Potyrailo, R. A., Hobbs, S. E., Hieftje, G. M., "Optical waveguide sensors in analytical chemistry: today's instrumentation, applications and trends for future development", Fresenius J. Anal. Chem., 362, 349-373, 1998.

FIG. 2 illustrates an alternative sensing system arrangement. Instead of using fiber optics for coupling laser light to a photonic crystal fiber as shown in FIG. 1, the sensing system 110 of FIG. 2 utilizes direct coupling of the laser light to the photonic crystal fiber 22. Specifically, the sensing system 110 includes an input housing 121 enclosing a laser 111 in direct optical communication with a lens 16 in an integrated lens housing 114. The integrated lens housing 114 differs from the integrated lens housing 14 in the positioning of the lens 16. The photonic crystal fiber 22 is housed within an enclosure 150, while the detecting portion of the sensing system 110 is housed within a detector housing 138. The detector housing 138 includes an integrated lens housing 130 having a lens 32 in direct optical communication with a filter 40 and a detector 44. The integrated lens housing 130 differs from the integrated lens housing 30 in the positioning of the lens 32. In the sensing systems 10 and 110 of FIGS. 1 and 2, gas samples enter the photonic crystal fiber 22, and Raman photons guided in the direction of propagation of the laser beam (forward Raman scattering) are collected at the exit end $22_b$ of the photonic crystal fiber 22 and used for quantitative measurements of the target chemical concentration.

FIG. 3 illustrates an alternative sensing system 210, which unlike the previously described sensing systems 10 and 110 utilizes reflection and not transmission in its detection of homonuclear diatomic molecules. The sensing system 210 includes a pump laser 211 in optical communication with collimating optics 232 through a fiber optic cable 212. The laser light exits the collimating optics 232 and enters a splitter 233. The splitter 233 is designed to transmit the excitation frequency to a collimating optics housing 252 and reflect returning light at different energies to a photodetector 264. The collimating optics housing 252 includes a lens 254, focusing optics 256 and an end of the photonic crystal fiber 22. The housing 252 further includes an inlet 18 and an outlet 34 for a fluidic medium, such as natural gas. The opposite end of the photonic crystal fiber 22 (the end not within the housing 252) is in optical communication with a mirror 258, which is imbued with high reflectivity at the target chemical Stokes peak spectral position. Gas samples enter the photonic crystal fiber 22, and Raman photons guided in the opposite direction of propagation of the laser (backward Raman scattering) are collected at the exit end 22 (the end not within the housing 252) of the photonic crystal fiber 22. The scattered light traverses the focusing optics 256 and collimating optics 254. The splitter 233 redirects the scattered light through a filter 260 and focusing optics 262 to the photodetector 264. The selected wavelengths can then be used for quantitative measurements of the target chemical concentration. The mirror 258 can be used to enhance the backward scattered photons by placing it at the exit end 22 (the end not within the housing 252) of the fiber 22. If the mirror 258 is designed to be transmissive at the laser wavelength, it could also act as a Rayleigh filter, assuming that little laser light is reflected back as it is coupled to the photonic crystal fiber 22.

Figure 5:
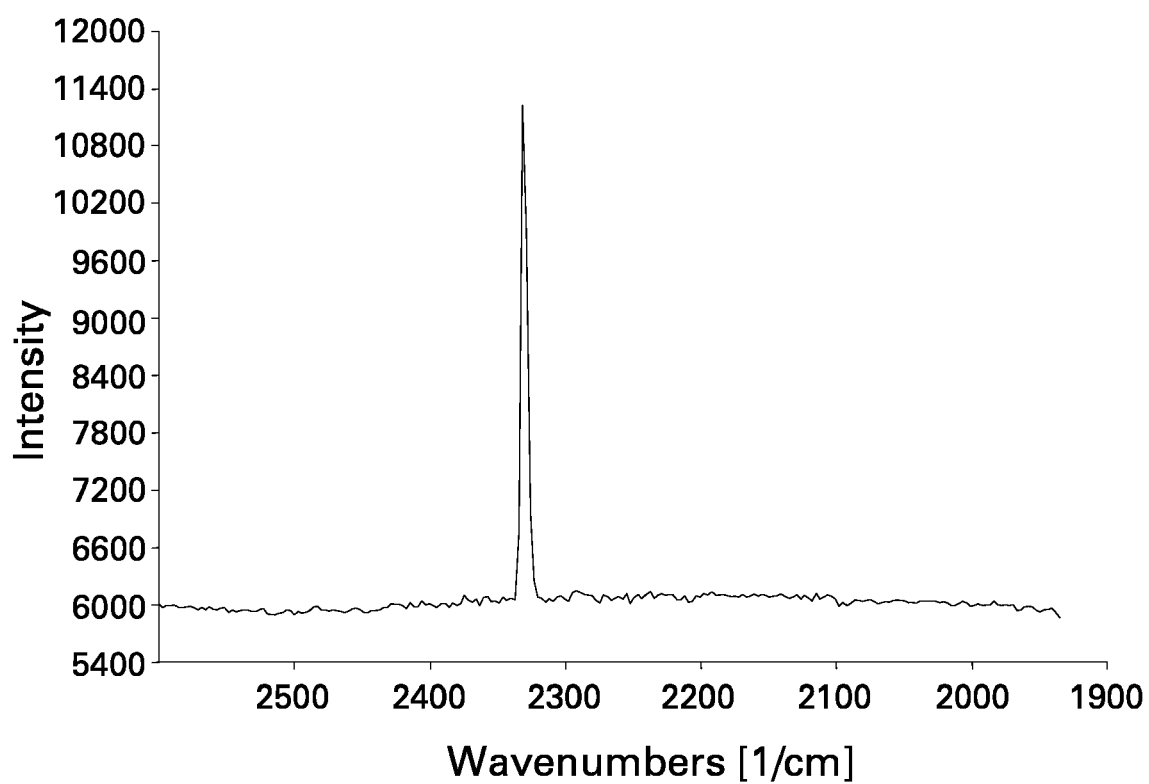
FIG. 5 illustrates a Raman spectrum of air at one atmosphere.
Figure 6:
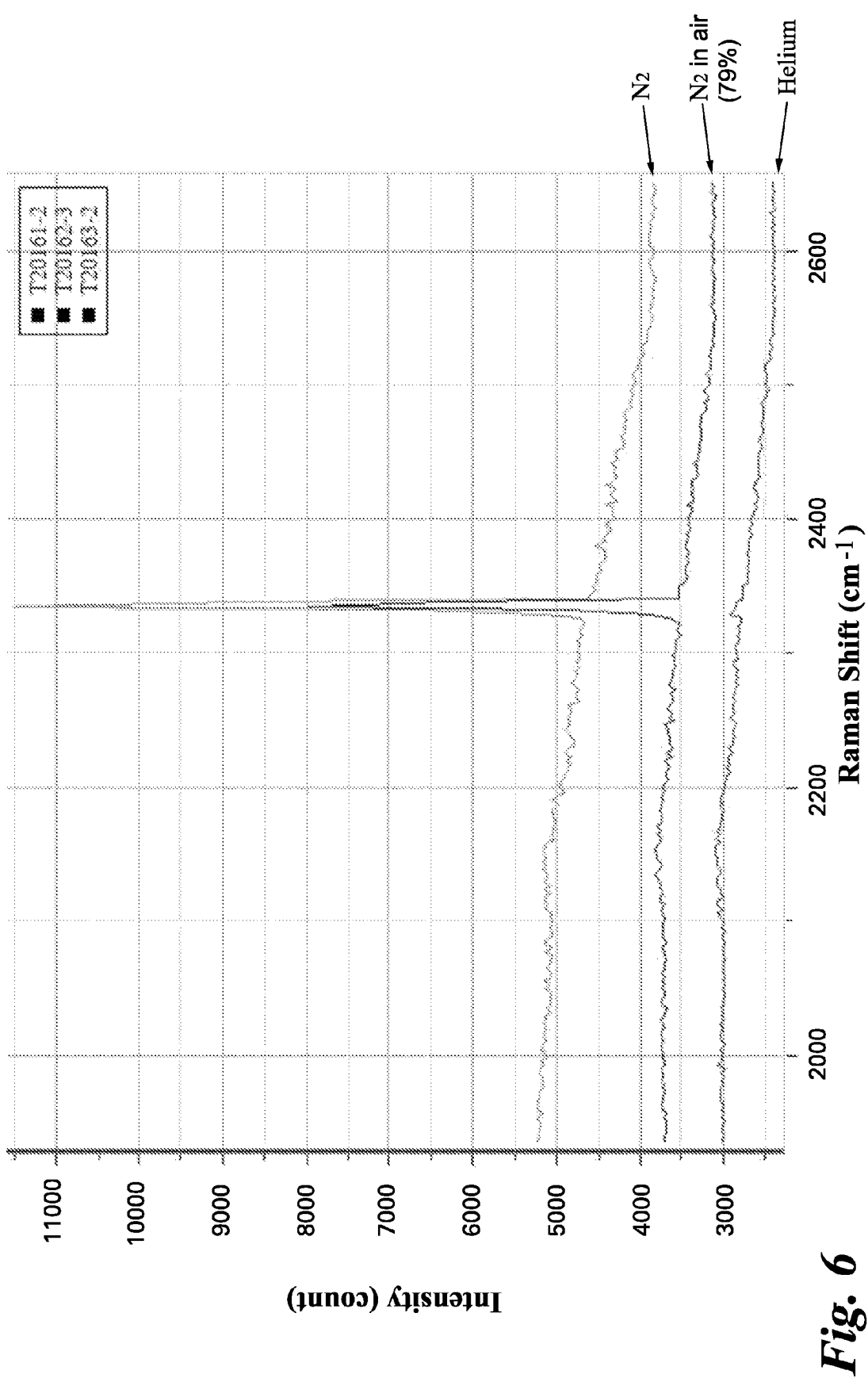
FIG. 6 illustrates Raman spectra of nitrogen gas, nitrogen gas in air, and helium.

FIG. 5 illustrates the Raman spectra of air at one atmosphere. As you can see, there is a spike in the spectra at 2331 $cm^{-1}$. The spike in the spectra corresponds to nitrogen found in the air. Compared to measurements done without a photonic bandgap fiber, a typical enhancement ratio of a few thousand has been demonstrated. FIG. 6 illustrates the Raman spectra of nitrogen gas, air, and helium. As is evident from the illustration, nitrogen peaks are found in the Raman spectra of the nitrogen gas and air, but not helium, at 2331 $cm^{-1}$.

Photonic crystal fibers can be designed to operate in the visible as well as the infrared parts of the spectrum. The transmission band and its width depend on the materials used to fabricate the fiber and the periodic hollow structure used to confine light in the air core. Fibers designed to transmit in the near infrared are typically useful for telecommunication as well as some gas sensing applications such as Near Infrared Absorption Spectroscopy (NIRS). NIR photonic crystal fibers can also be used for Raman detection of gases and fluids in general, but the Raman signals are much weaker and can be easily overwhelmed. In fact, Raman intensity is proportional to the inverse of the fourth power of the excitation wavelength. Thus, operating at longer wavelengths in the NIR has detrimental effects on the Raman signal and the analytical instrument sensitivity and detection accuracy if the objective is to design a gas analyzer. Embodiments of the invention include a photonic crystal fiber selected to transmit in the visible range, where Raman scattering is much stronger than in the NIR, and the bandwidth is chosen such that the laser excitation wavelength and the Stokes lines of the target analyte molecules fall within the transmission band of the fiber. This enables utilization of the fiber in both forward and backward scattering modes where the Raman photons are either collected on the excitation laser launch side or the opposite side.

It should be appreciated that the emission of secondary radiation from a primary radiation excitation at a photonic crystal fiber may be used in the optical measuring at least one analyte in a sample. For example, the primary radiation excitation of light into a photonic crystal fiber may be done at excitation conditions that control non-analyte related emission of secondary radiation. The secondary radiation may be, for example, a fluorescence emission, photoluminescence emission, or a Raman emission from material of the photonic crystal fiber. It should be further appreciated that the emission of secondary radiation may be reduced by natural attenuation of the photonic crystal fiber in spectral regions where the emission of secondary radiation occurs. Also, detection of optical radiation upon interaction with the sample may be accomplished at either an excitation end of the photonic crystal fiber or its distal end. Further, an operational lifetime of the photonic crystal fiber may be lengthened by a surface treatment to reduce deposition effects of contaminants.

Additionally, the emission of secondary radiation may be used to improve the accuracy of measurements. For example, by providing corrections for aging of a light source, repositioning effects, or partial contamination of the optical elements the accuracy of measurements may be improved. Corrections are provided using spectral ratiometric or spectral multivariate corrections. In spectral ratiometric corrections, the intensity of the secondary emission at a wavelength that corresponds to the secondary emission mostly from an analyte (for example nitrogen gas) is normalized by the intensity of the secondary emission at a wavelength that corresponds to the secondary emission mostly from the photonic crystal fiber.

In spectral multivariate corrections, the spectral profile (several wavelengths) of the secondary emission at a wavelength that corresponds to the secondary emission mostly from an analyte (for example nitrogen gas) is corrected by the spectral profile of the secondary emission that corresponds to the secondary emission mostly from the photonic crystal fiber. The measurements that may have their accuracy improved may include, for example, quantitative determinations, such as univariate analysis or multivariate analysis.

EXAMPLE

Figure 7:
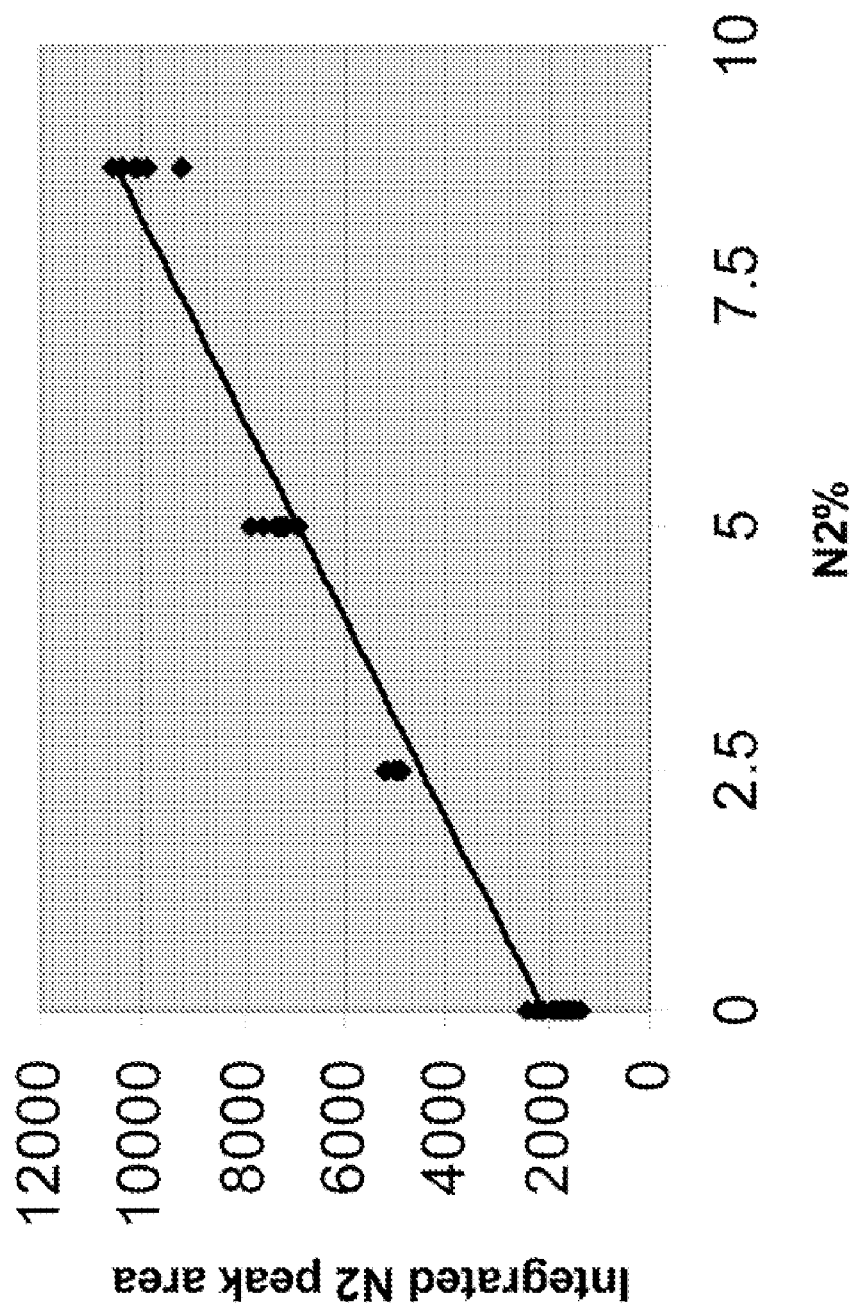
FIG. 7 illustrates a calibration curve constructed from multiple measurements of Raman spectra of nitrogen when different concentrations of nitrogen were introduced into a photonic crystal fiber.
Figure 8:
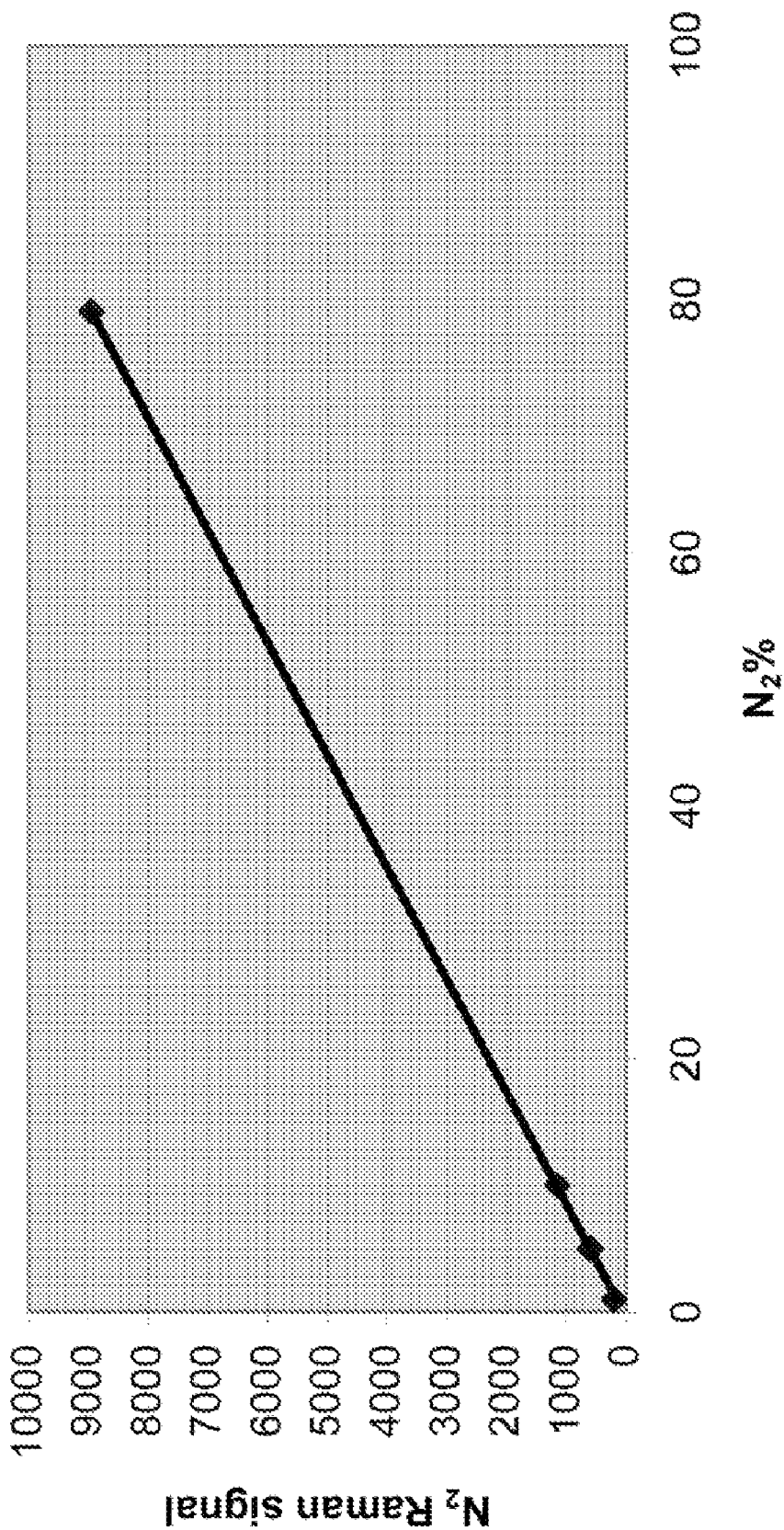
FIG. 8 illustrates another calibration curve for nitrogen gas concentrations were introduced into another photonic crystal fiber.

For quantitation of nitrogen using a photonic fiber, a Raman microscope has been employed. Raman excitation was achieved with an argon ion laser emitting at 514 nm laser (16 mW). For experiments, a 4-centimeter long photonic crystal fiber was used. FIG. 7 illustrates the calibration curve constructed from multiple measurements of Raman spectra of nitrogen gas when different concentrations of nitrogen gas were introduced into the photonic crystal fiber. FIG. 8 illustrates a calibration curve for a broader range of nitrogen gas concentrations than in FIG. 7 that were introduced into a longer photonic crystal fiber than used for FIG. 7.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. For example, another embodiment includes light being collected from the fiber and transmitted through, or reflected off of, a dispersive element and detected by a CCD. This arrangement enables collection of a spectrum. This differs from other embodiments that require collection of a limited spectral range through a filter. This embodiment, unlike the other embodiments described herein, will work for quantitative determinations being some measure of the baseline. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected by Letters Patent of the United States is:

1. A method for sensing homonuclear diatomic molecules, comprising:
    transmitting light from a light source through a hollow-core wave-guiding device that exhibits a low attenuation at predetermined operating optical frequencies;
    introducing a gaseous medium between the light source and the hollow-core wave-guiding device; and
    detecting homonuclear diatomic molecules within the gas.

2. The method of claim 1, wherein said transmitting light comprises transmitting light through a photonic crystal fiber.

3. The method of claim 1, wherein the homonuclear diatomic molecules comprise nitrogen.

4. A method of detecting comprising:
    transmitting light from a light source through a hollow-core wave-guiding device;
    introducing a material between the light source and the hollow-core wave-guiding device; and
    detecting a homonuclear diatomic molecule within the material.

5. The method of claim 4, wherein the material comprises one of a flowing liquid, a gaseous medium, and a fluidic medium.

6. The method of claim 4, wherein the material comprises natural gas.

7. The method of claim 4, wherein the homonuclear diatomic molecule comprises nitrogen.

8. The method of claim 4, wherein the hollow-core wave-guiding device comprises a photonic crystal fiber.

9. The method of claim 4, wherein the hollow-core wave-guiding device exhibits a low attenuation at predetermined operating optical frequencies.

10. The method of claim 4, wherein the material comprises air.

\* \* \* \* \*

UNITED STATES PATENT AND TRADEMARK OFFICE
CERTIFICATE OF CORRECTION

PATENT NO. : 7,595,882 B1  Page 1 of 1
APPLICATION NO. : 12/102079
DATED : September 29, 2009
INVENTOR(S) : Chen et al.

It is certified that error appears in the above-identified patent and that said Letters Patent is hereby corrected as shown below:

On the Face Page, in Field (73), under "Assignee", in Column 1, Line 1, delete "Geneal" and insert -- General --, therefor.

In Column 1, Lines 53-54, delete "$4.5 \times 10^-{}_5$." and insert -- $4.5 \times 10^{-5}$. --, therefor.

Signed and Sealed this

Twenty-second Day of June, 2010

David J. Kappos
*Director of the United States Patent and Trademark Office*